(12) United States Patent
Gauvry et al.

(10) Patent No.: US 9,920,037 B2
(45) Date of Patent: Mar. 20, 2018

(54) DIARYL ISOXAZOLINE COMPOUND

(71) Applicant: Elanco Tiergesundheit AG, Indianapolis, IN (US)

(72) Inventors: Noëlle Gauvry, Kembs (FR); Thomas Goebel, Lörrach (DE); Steve Nanchen, Basel (CH); Jean-Luc Perret, Saint-Aubin (FR); Ulrich Roos, Lörrach (DE); Sandra Schorderet Weber, Neuchâtel (CH)

(73) Assignee: Elanco Tiergesundheit AG, Basel (CH)

( * ) Notice: Subject to any disclaimer, the term of this patent is extended or adjusted under 35 U.S.C. 154(b) by 0 days.

(21) Appl. No.: 15/517,731

(22) PCT Filed: Nov. 6, 2015

(86) PCT No.: PCT/US2015/059371
§ 371 (c)(1),
(2) Date: Apr. 7, 2017

(87) PCT Pub. No.: WO2016/077158
PCT Pub. Date: May 19, 2016

(65) Prior Publication Data
US 2017/0240536 A1     Aug. 24, 2017

(30) Foreign Application Priority Data
Nov. 10, 2014   (EP) ..................................... 14192483

(51) Int. Cl.
*C07D 413/04*   (2006.01)

(52) U.S. Cl.
CPC ................................. *C07D 413/04* (2013.01)

(58) Field of Classification Search
CPC .................................................... C07D 413/04
See application file for complete search history.

(56) References Cited

FOREIGN PATENT DOCUMENTS

WO        2010/070068 A2    6/2010

*Primary Examiner* — Sudhakar Katakam
(74) *Attorney, Agent, or Firm* — Joseph M. Pletcher

(57) ABSTRACT

The present invention concerns compounds of formula (I) or an N-oxide or salt thereof and their use for controlling parasites in and on warm-blooded animals or fish.

(I)

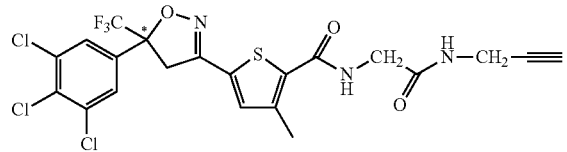

5 Claims, No Drawings

DIARYL ISOXAZOLINE COMPOUND

The present invention relates to novel diaryl isoxazoline compounds and their use in the control of ectoparasites, especially insects and acari, on non-human animals, especially productive livestock, domestic animals and fish, and furthermore pesticidal compositions which contain the compounds.

WO2010/070068 discloses diaryl isoxazoline compounds of the formula

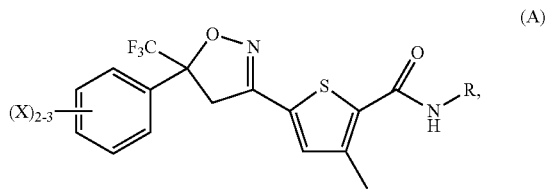

wherein X is, for example, halogen and R has various meanings, for example, alkynylcarbamoylalkyl. The compounds of this document are said to be effective against all kinds of ectoparasites.

It has now been found that certain novel diaryl isoxazoline compounds are efficient in the control of ectoparasites at low concentrations while being tolerated by the animals and being environmentally safe.

SUMMARY OF THE INVENTION

The present invention therefore according to one aspect concerns a compound of formula

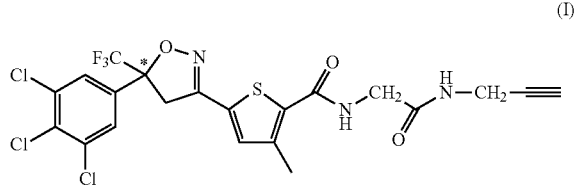 [SMILES: C#CCNC(=O)CNC(=O)c1sc(C2=NOC(c3cc(Cl)c(Cl)c(Cl)c3)(C(F)(F)F)C2)cc1C]

or an N-oxide or salt thereof.

Further embodiments of the invention concern parasiticidal compositions containing an above compound of formula (I) or an N-oxide or salt thereof and their use in the reduction or elimination of ectoparasites in or on animals.

DETAILED DESCRIPTION

The novel compound of formula (I) has an asymmetrical C-atom, indicated with an asterix in formula (I) above. The present invention concerns mixtures of the two enantiomers, including racemic mixtures thereof, and the corresponding isolated enantiomers. A preferred embodiment relates to the S-enantiomer of the compound of formula (I) whose activity against sea lice exceeds that of the corresponding R-enantiomer.

The compound of formula (I) may be prepared by processes well known to one of ordinary skill in the art, for example in analogy to the processes disclosed in WO2010/070068.

Enantiomer separation of a compound of formula (I) may be performed in a manner known per se, for example by simple recrystallization, kinetic resolution, by means of biotechnological methods (whole cells, enzymes, etc.), by chromatographic methods, or by methods that are based on the difference of physicochemical properties of diastereomers prepared by reversible addition of an optically pure reagent.

Synthetic methods for the preparation of N-oxides of heterocyclic rings and tertiary amines are very well known by one skilled in the art including the oxidation of heterocyclic rings and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethyl dioxirane. These methods for the preparation of N-oxides have been extensively described and reviewed in the literature.

One skilled in the art recognizes that because of the environment and under physiological conditions salts of chemical compounds are in equilibrium with their corresponding nonsalt forms, salts share the biological utility of the non-salt forms. Thus a wide variety of salts of the compounds of formula (I) are useful for control of invertebrate pests (i.e. are veterinarily or agriculturally acceptable). Accordingly, the present invention comprises compounds selected from formula (I), N-oxides and veterinary acceptable and agriculturally suitable salts thereof.

The compound of the formula (I) or an enantiomer, N-oxide or salt thereof according to the invention are notable for their broad activity spectrum and are valuable active ingredients for use in pest control. They are particularly suitable in the control of ectoparasites and to a certain extent also for controlling endoparasites on and in animals and in the hygiene field, whilst being well tolerated by vertebrates such as warm-blooded animals and fishes.

Animals in the context of the invention are understood to include vertebrates. The term vertebrate in this context is understood to comprise, for example fish, amphibians, reptiles, birds, and mammals including humans. One preferred group of vertebrates according to the invention comprises warm-blooded animals including farm animals, such as cattle, horses, pigs, sheep and goats, poultry such as chickens, turkeys, guinea fowls and geese, fur-bearing animals such as mink, foxes, chinchillas, rabbits and the like, as well as companion animals such as ferrets, guinea pigs, rats, hamster, cats and dogs, and also humans. A further group of preferred vertebrates according to the invention comprises fish including salmonids, for example salmon, trout or whitefish.

In the context of the present invention, ectoparasites are understood to be in particular insects, acari (mites and ticks), and crustaceans (sea lice). These include insects of the following orders: Lepidoptera, Coleoptera, Homoptera, Hemiptera, Heteroptera, Diptera, Dictyoptera, Thysanoptera, Orthoptera, Anoplura, Siphonaptera, Mallophaga, Thysanura, Isoptera, Psocoptera and Hymenoptera. However, the ectoparasites which may be mentioned in particular are those which trouble humans or animals and carry pathogens, for example flies such as *Musca domestica, Musca vetustissima, Musca autumnalis, Fannia canicularis, Sarcophaga carnaria, Lucilia cuprina, Lucilia sericata, Hypoderma bovis, Hypoderma lineatum, Chrysomyia chloropyga, Dermatobia hominis, Cochliomyia hominivorax, Gasterophilus intestinalis, Oestrus ovis*, biting flies such as *Haematobia irritans irritans, Haematobia irritans exigua, Stomoxys calcitrans*, horse-flies (Tabanids) with the subfamilies of Tabanidae such as *Haematopota* spp. (e.g. *Haematopota pluvialis*) and *Tabanus* spp, (e.g.*Tabanus nigrovittatus*) and

*Chrysopsinae* such as *Chrysops* spp. (e.g. *Chrysops caecutiens*); *Hippoboscids* such as *Melophagus ovinus* (sheep ked); tsetse flies, such as *Glossinia* spp,; other biting insects like midges, such as Ceratopogonidae (biting midges), Simuliidae (Blackflies), Psychodidae (Sandflies); but also blood-sucking insects, for example mosquitoes, such as *Anopheles* spp, *Aedes* spp and *Culex* spp, fleas, such as *Ctenocephalides felis* and *Ctenocephalides canis* (cat and dog fleas), *Xenopsylla cheopis, Pulex irritans, Ceratophyllus gallinae, Dermatophilus penetrans*, blood-sucking lice (Anoplura) such as *Linognathus* spp, *Haematopinus* spp, *Solenopotes* spp, *Pediculus humanis*; but also chewing lice (Mallophaga) such as *Bovicola (Damalinia) ovis, Bovicola (Damalinia) bovis* and other *Bovicola* spp. Ectoparasites also include members of the order Acarina, such as mites (e.g. *Chorioptes bovis, Cheyletiella* spp., *Dermanyssus gallinae, Ortnithonyssus* spp., *Demodex canis, Sarcoptes scabiei, Psoroptes ovis* and *Psorergates* spp. and ticks. Known representatives of ticks are, for example, *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest vertebrates, for example warm-blooded animals including farm animals, such as cattle, horses, pigs, sheep and goats, poultry such as chickens, turkeys, guineafowls and geese, fur-bearing animals such as mink, foxes, chinchillas, rabbits and the like, as well as companion animals such as ferrets, guinea pigs, rats, hamster, cats and dogs, but also humans and fishes.

The compound of formula (I) or an enantiomer, N-oxide or salt thereof are also effective in the control of fish-parasitic crustaceans, also called sea lice, whilst being well tolerated by fish. These fish-parasitic crustaceans include the Family Caligidae with representative genus *Dissonus, Caligus* (i.e. *C. curtus, C. elongatus, C. clemensi, C. rogercresseyii*), and *Lepeophtheirus* (i.e. *L. salmonis*); Families Cecropidae, Dichelesthiidae, Lernaeopodidae with representative genus *Salmincola*; Families Pandaridae, Pennellidae with representative genus *Lernaeocera* and *Pennella*; and Family Sphyriidae; Family Lernaeidae with representative genus *Lernaea*; Families Bomolochidae, Chondracanthidae, Ergasilidae and Philichthyidae; Family Argulidae with representative genus *Argulus* (i.e. *A. foliaceus*).

The compound of the formula (I) or an enantiomer, N-oxide or salt thereof according to the invention are also active against all or individual development stages of animal pests showing normal sensitivity, as well as those showing resistance to widely used parasiticides. This is especially true for resistant insects and members of the order Acarina. The insecticidal, ovicidal and/or acaricidal effect of the active substances of the invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%.

The compounds of the formula (I) or an enantiomer, N-oxide or salt thereof can also be used against hygiene pests, especially of the order Diptera of the families Muscidae, Sarcophagidae, Anophilidae and Culicidae; the orders Orthoptera, Dictyoptera (e.g. the family Blattidae (cockroaches), such as *Blatella germanica, Blatta orientalis, Periplaneta americana*) and Hymenoptera (e.g. the families Formicidae (ants) and Vespidae (wasps).

A compound of the formula (I) or an enantiomer, N-oxide or salt thereof also have sustainable efficacy on parasitic mites and insects of plants. In the case of spider mites of the order Acarina, they are effective against eggs, nymphs and adults of Tetranychidae (*Tetranychus* spp. and *Panonychus* spp.).

They have high activity against sucking insects of the order Homoptera, especially against pests of the families Aphididae, Delphacidae, Cicadellidae, Psyllidae, Loccidae, Diaspididae and Eriophydidae (e.g. rust mite on citrus fruits); the orders Hemiptera, Heteroptera and Thysanoptera, and on the plant-eating insects of the orders Lepidoptera, Coleoptera, Diptera and Orthoptera They are similarly suitable as a soil insecticide against pests in the soil.

The compound of formula (I) or an enantiomer, N-oxide or salt thereof are therefore effective against all stages of development of sucking insects and eating insects on crops such as cereals, cotton, rice, maize, soya, potatoes, vegetables, fruit, tobacco, hops, citrus, avocados and other crops.

The compound of formula I or an enantiomer, N-oxide or salt thereof are also effective against plant nematodes of the species *Meloidogyne, Heterodera, Pratylenchus, Ditylenchus, Radopholus, Rizoglyphus* etc.

The pesticidal activity of the compound of formula (I) or an enantiomer, N-oxide or salt thereof according to the invention corresponds to a mortality rate of at least 50-60% of the pests mentioned, more preferably to a mortality rate over 90%, most preferably to 95-100%. The compound of formula (I) or an enantiomer, N-oxide or salt thereof are preferably employed internally and externally in unmodified form or preferably together with the adjuvants conventionally used in the art of formulation and may therefore be processed in a known manner to give, for example, liquid formulations (e.g. spot-on, pour-on, spray-on, emulsions, suspensions, solutions, emulsifiable concentrates, solution concentrates), semi-solid formulations (e.g. creams, ointments, pastes, gels, liposomal preparations) and solid preparations (e.g. food additives tablets including e.g. capsules, powders including soluble powders, granules, or embeddings of the active ingredient in polymeric substances, like implants and microparticles). As with the compositions, the methods of application are selected in accordance with the intended objectives and the prevailing circumstances.

The formulation, i.e. preparations containing the active ingredient of formula (I) or an enantiomer, N-oxide or salt thereof according to the invention, and one or more pharmaceutically or veterinary acceptable excipients, for example a solid, semi-solid or liquid adjuvant, are produced in a manner known per se, for example by intimately mixing, kneading or dispersing the active ingredients with compositions of excipients, whereby the physiological compatibility of the formulation excipients must be taken into consideration.

The solvents in question may be: alcohols (aliphatic and aromatic), such as benzylalcohol, ethanol, propanol, isopropanol or butanol, fatty alcohols, such as oleyl alcohol and glycols and their ethers and esters, such as glycerin, propylene glycol, dipropylene glycol ether, ethylene glycol, ethylene glycol monomethyl or -ethyl ether and butyl dioxytol, carbonates, such as propylene carbonate, ketones, such as cyclohexanone, isophorone or diacetanol alcohol and polyethylene glycols, such as PEG 300. In addition, the compositions may comprise strong polar solvents, such as N-methyl-2-pyrrolidone, dimethyl sulfoxide or dimethylformamide, or water, fatty acid esters, such as ethyl oleate or isopropylpalmitate, vegetable oils, such as rape, castor, coconut, or soybean oil, synthetic mono-, di-, triglycerides like e.g. glyceryl monostearate and medium chain triglycerides and also, if appropriate, silicone oils. The mentioned ingredients may also serve as carrier for particulate application forms.

As ointment base resp. structure building ingredients the following excipients may be used: Petroleum based substances, such as Vaseline or paraffines, bases made from wool fat, like e.g. lanolin or lanolin alcohols, polyethylene glycols like e.g. macrogols and lipid bases like e.g. phospholipids or triglycerids, such as hydrogenated vegetable oils.

The use of emulsifiers, wetting agents and spreading agents may also be required, in general, lecithins like soy lecithin, salts of fatty acids with alkaline earth and alkali metals, alkyl sulfates like sodium cetylstearyl sulphate, cholates, fatty alcohols like cetyl alcohol, sterols like cholestesterol, polyoxyethylene sorbitan fatty acid esters like polysorbate 20, sorbitan fatty acid esters like sorbitan mono laureate, fatty acid esters and fatty alcohol ethers of polyoxyethylene like poloxyl oleyl ether, polyoxypropylene polyoxyethylene block copolymers as e.g. Pluronic™, saccharose esters like saccharose distearate, polyglyceryl fatty acid esters like polyglycerol oleate and fatty acid esters like e.g. ethyl oleate or isopropylmyristate.

The formulations may also include gelifying and stiffening agents, like e.g. polyacrylic acid derivatives, cellulose ethers, polyvinyl alcohols, polyvinylpyrrolidons and fine disperse silicium dioxide.

As polymeric agents with controlled release properties, may be applied derivatives made by e.g. polylactic acid, polylactic coglycolic acid, poly orthoester, polyethylene carbonate, poly anhydrids and starch and PVC based matrices.

The addition of penetration enhancers like ketones, sulfoxides, amides, fatty acid esters and fatty alcohols may be necessary.

Also preservatives like sorbic acid, benzyl alcohol and parabenes, and antioxidants as e.g. alpha tocopherol may be added.

The active ingredient or combinations of the active ingredient may also applied in capsules, like hard gelatine capsules or soft capsules.

The binders for tablets and boli may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), lubricants (e.g. magnesium stearate), glidants (e.g. colloidal silicon dioxide) and disintegrants (e.g. cellulose derivatives) and acid resistant coatings, like e.g. acrylic acid esters.

The compound of formula (I) or an enantiomer, N-oxide or salt thereof according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. For example, in case of a compound of formula (I) having a particular efficacy as adulticide, i.e. since it is effective in particular against the adult stage of the target parasites, the addition of a pesticide which instead attack the juvenile stages of the parasites may be very advantageous, or vice versa. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula (I).

Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broad-band insecticides, broad-band acaricides and nematicides; and also the well known anthelminthics and insect- and/or acarid-deterring substances, said repellents or detachers. Non-limitative examples of suitable insecticides and acaricides are mentioned in WO 2009/071500, compounds Nos. 1-284 on pages 18-21. Non-limitative examples of suitable anthelminthics are mentioned in WO 2009/071500, compounds (A1)-(A31) on page 21. Non-limitative examples of suitable repellents and detachers are mentioned in WO 2009/071500, compounds (R1)-(R3) on page 21 and 22. Non-limitative examples of suitable synergists are mentioned in WO 2009/071500, compounds (S1)-(S3) on page 22.

The said partners in the mixture are best known to specialists in this field. Most are described in various editions of the Pesticide Manual, The British Crop Protection Council, London, and others in the various editions of The Merck Index, Merck & Co., Inc., Rahway, N.J., USA or in patent literature.

As a consequence of the above details, a further aspect of the present invention relates to a combination preparation for the control of parasites on vertebrates, in particular on warm-blooded animals or on fishes, characterised in that it contains, in addition to a compound of formula (I), at least one further active ingredient having the same or different sphere of activity and at least one physiologically acceptable carrier. The present invention is not restricted to two-fold combinations.

As a rule, the insecticidal and acaricidal compositions according to the invention contain 0.1 to 99% by weight, especially 0.1 to 95% by weight of an active ingredient of formula (I), 99.9 to 1% by weight, especially 99.8 to 5% by weight of a solid or liquid admixture, including 0 to 25% by weight, especially 0.1 to 25% by weight of a surfactant.

Application of the compositions according to the invention to the animals to be treated may take place topically, perorally, parenterally or subcutaneously, the composition being present, for example, in the form of solutions, emulsions, suspensions, (drenches), powders, tablets, boli, capsules, chewable treats, collars, eartags and pour-on formulations.

Preferred topical formulations are understood to refer to a ready-to-use solution in form of a spot-on, pour-on or spray-on formulation often consisting of a dispersion or suspoemulsion or a combination of active ingredient and spreading auxiliaries. The expression spot-on or pour-on method is understood to refer to a ready-to-use concentrate intended to be applied topically and locally on the animal. This sort of formulation is intended to be applied directly to a relatively small area of the animal, preferably on the animal's back and breech or at one or several points along the line of the back and breech. It is applied as a low volume of about 0.05 to about 1 ml per kg, preferably about 0.1 ml per kg, with a total volume from 0.1 to 100 ml per animal, preferably limited to a maximum of about 50 ml. However, it goes without saying that the total volume has to be adapted to the animal that is in need of the treatment and will clearly be different, for example, in young cats and in cattle. These pour-on and spot-on formulations are designed to spread all around the animal giving protection or treatment to almost any part of the animal. Even so the administration is carried out by applying a swab or spray of the pour-on or spot-on formulation to a relatively small area of the coat, one observes that from the active substance is dispersed almost automatically over wide areas of the fur owing to the spreading nature of the components in the formulation and assisted by the animal's movements.

Pour-on or spot-on formulations suitably contain carriers, which promote rapid dispersement over the skin surface or in the coat of the host animal, and are generally regarded as spreading oils. Suitable carriers are e.g. oily solutions; alcoholic and isopropanolic solutions such as solutions of 2-octyldodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol or synthetic triglycerides.

The oily solutions include e.g. vegetable oils such as olive oil, groundnut oil, sesame oil, pine oil, linseed oil or castor oil. The vegetable oils may also be present in epoxidised form. Paraffins and silicone oils may also be used.

A pour-on or spot-on formulation generally contains 1 to 98.9% by weight of a compound of formula (I), 0.1 to 80% by weight of dispersing agent and 1 to 98.9% by weight of solvent.

The pour-on or spot-on method is especially advantageous for use on herd animals such as cattle, horses, sheep or pigs, in which it is difficult or time-consuming to treat all the animals orally or by injection. Because of its simplicity, this method can of course also be used for all other animals, including individual domestic animals or pets, and is greatly favoured by the keepers of the animals, as it can often be carried out without the specialist presence of the veterinarian.

Whereas it is preferred to formulate commercial products as concentrates, the end user will often use dilute formulations. However, this depends on the mode of administration. Orally administered products are most often used in diluted form or as feed additives, whereas commercial pour-on and spot-on formulations are normally ready-to-use concentrates.

Such compositions may also contain further additives, such as stabilisers, anti-foaming agents, viscosity regulators, binding agents or tackifiers, as well as other active ingredients, in order to achieve special effects.

Insecticidal and acaricidal compositions of this type, which are used by the end user, similarly form a constituent of the present invention.

In each of the processes according to the invention for pest control or in each of the pest control compositions according to the invention, the active ingredients of formula (I) can be used in all of their steric configurations or in mixtures thereof.

The invention also includes a method of prophylactically protecting animals, especially productive livestock, domestic animals and pets, against parasitic helminths, which is characterised in that the active ingredients of formula (I) or the active ingredient formulations prepared therefrom are administered to the animals as an additive to the feed, or to the drinks or also in solid or liquid form, orally or by injection or parenterally. The invention also includes the compounds of formula (I) according to the invention for usage in one of the said processes.

The following examples illustrate the invention, the term active ingredient representing any substance as described in the preparation examples. %=percent by weight. The starting materials are known and partially commercially available or may be produced in analogy to methods known per se.

Analysis of the purified sample is in each case done using a Waters Autopurification (HPLC/MS) system with a reversed phase column (Daisogel SP-120-ODS-AP 5 µm, 150×3 mm) from Bischoff, Leonberg, Germany. The samples are characterized by m/z and retention time. The above-given retention times relate in each case to the use of a solvent system comprising two different solvents, solvent A: $H_2O$+0.01% HCOOH, and solvent B: $CH_3CN$+0.01% HCOOH). Said two solvents A and B are employed at a flow rate of 2.00 ml/min with a time-dependent gradient as given in the Table:

| Time [min] | A [%] | B [%] |
|---|---|---|
| 0.5 | 10 | 90 |
| 1.0 | 26 | 74 |
| 1.5 | 40 | 60 |
| 2.0 | 53 | 47 |
| 2.5 | 64 | 36 |
| 3.0 | 74 | 26 |
| 3.5 | 81 | 19 |
| 4.0 | 87 | 13 |
| 4.25 | 90 | 10 |
| 4.5 | 92 | 8 |
| 4.75 | 93 | 7 |
| 5.0 | 94 | 6 |
| 5.5 | 95 | 5 |
| 6.5 | 95 | 5 |

EXAMPLE 1

Preparation of the Racemic Compound of Formula (I)

(i) Thiophene carboxylic acid of formula (II)

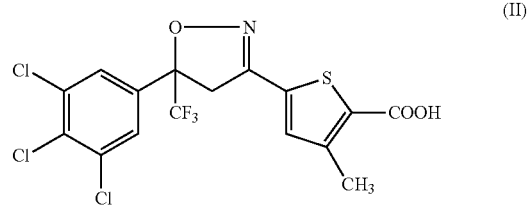 [SMILES: Cc1cc(C2=NOC(c3cc(Cl)c(Cl)c(Cl)c3)(C(F)(F)F)C2)sc1C(=O)O]

is synthesized according to the procedure described in Example 1 of patent application WO2014/090918.

(ii) DIPEA (116 mL) and propargylamine (18.2 g) are added to a solution of N-(tert-butoxycarbonyl)glycine (52.5 g) and TBTU (106 g) in dichloromethane (800 mL) at 0° C. After 18 hours at room temperature, the reaction mixture is concentrated in vacuo. The residue is taken in water and ethyl acetate. The phases are separated and the organic phase is washed with water, dried over MgSO$_4$ and concentrated in vacuo. The crude product is stirred in a mixture of dichloromethane, ethyl acetate and heptan (3:2:4) and filtered to yield tert-butyl N-[2-oxo-2-(prop-2-ynylamino)ethyl]carbamate used without further purification.

(iii) Trifluoroacetic acid (370 mL) is added dropwise to a solution of tert-butyl N-[2-oxo-2-(prop-2-ynylamino)ethyl] carbamate (51 g) in dichloromethane (1 L). After 15 hours at room temperature, the reaction mixture is concentrated in vacuo. The crude solid is suspended in diethyl ether and filtered to yield 2-amino-2-propyn-1-yl-acetamide trifluoroacetate salt (52 g) as a beige solid.

(iv) Thionyl chloride (2.8 mL) is added to a solution of thiophene carboxylic acid (II) (5.9 g) in toluene (60 mL). After 30 minutes at reflux, the reaction mixture is cooled down and concentrated in vacuo. The crude product is dissolved in dichloromethane (70 mL) and 2-amino-N-prop-2-ynyl-acetamide trifluoroacetate salt (3.4 g) and DIPEA (5.6 mL) are added. After 18 hours at room temperature, water is added to the reaction mixture. The phases are separated and the organic phase is washed with water, dried over MgSO$_4$ and concentrated in vacuo. The residue is dissolved in ethyl acetate/heptan (1:1) and filtered through a pad of silica gel. The product is crystallized with ethyl acetate and diisopropyl ether to yield the racemic compound of formula (I) (5.8 g) as a light beige solid. MS (HPLC/MS): 552 (MH$^+$). Retention time: 3.98 min. M.p. : 151-153° C.

EXAMPLE 2

Preparation of the (S)-enantiomer of the Compound of Formula (I)

(i) The (S)-enantiomer of the thiophene carboxylic acid of formula (II) is synthesized according to the procedure described in Example 2 of patent application WO2014/090918 and isolated as a salt of (R)-1-(4-methylphenyl)ethylamine.

(ii) 3.81 kg of the (S)-isoxazoline thiophene carboxylic acid salt from Example 2 (i) in 34 kg of toluene are heated to 60° C. The hot solution is extracted three times with 13 kg of 1 molar HCl solution. About 50% of the organic layer is then distilled off under vacuum. Following the addition of further 16 kg of toluene the mixture is heated to 110° C. and 2.07 kg of thionyl chloride are dosed slowly to the reaction mixture. Following stiffing for an additional hour 37 kg of toluene are removed under vacuum. The reaction mixture is cooled to ambient temperature, and 15 kg of dichloromethane are added.

(iii) The dichloromethane solution of step (ii) is added to a mixture of 1 kg of 2-amino-2-propyn-1-yl-acetamide hydrochloride and 2.06 kg of triethylamine in 15 kg of dichloromethane at 5° C. The reaction mixture is stirred for additional 2 hours and is then extracted with 4% hydrochloric acid, 8% sodium hydrogen carbonate and water. Most of the organic layer is then removed under vacuum, and 7 kg of tert-butylmethyl ether are added. The reaction mixture is kept at 25° C., and 14 kg of heptane are added slowly to precipitate the product. The crude product is isolated by filtration and is washed with 7 kg of heptane and dried at 45° C. under vacuo. Crystallization of the product may be performed as appropriate. M.p.: 139-140° C.

The enantiomeric purity of the compound has been determined by HPLC with a chiral column (Daicel Chiralpak IA-3, 150×4.6 mm). The above-given retention times relate in each case to the use of a solvent system comprising two different solvents, solvent A:heptane/ethanol 85:15, and solvent B:ethanol/dichloromethane 10:1. Said two solvents A and B are employed at a flow rate of 1.1 ml/min with an isocratic gradient 97% A-3% B during 20 min.

(S)-enantiomer of the compound of formula (I): single peak, retention time: 8.41 min Racemic compound of formula (I): two peaks, retention times: 8.41 min ((S)-enantiomer) and 12.90 min ((R)-enantiomer).

EXAMPLE 3

Activity in Vitro Against *Lepeophtheirus salmonis* at Copepodid Stage

Sea lice copepodids were used to seed a 96-well plate containing the test substances to be evaluated for antiparasitic activity. The racemic compound of formula (I) according to the present invention and the racemic compound No. 1.48 according to WO2010/070068, page 47 were tested by serial dilution in order to determine its minimal effective dose (MED). Copepodids were left in contact with each test compound diluted in sea water for 1 hour. They were then incubated in untreated sea water for 48 h. Efficacy against sea lice was then confirmed if no copepodid moved over a period of 80 seconds.

In this test the racemic compound of formula (I) according to the present invention showed 100% efficacy at a dose of as low as 0.16 ng/ml sea water. In strong contradiction thereto, the racemic compound No. 1.48 according to WO2010/070068, which is of formula

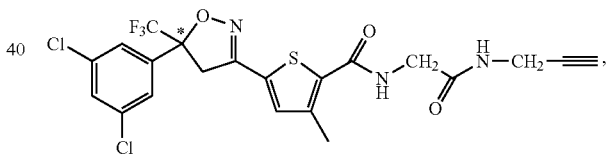

showed 0% efficacy at said concentration of 0.16 ng/ml sea water.

EXAMPLE 4

Activity in Vivo Against *Rhipicephalus sanguineus* Nymphs on Mongolian Gerbils (*Meriones unguiculatus*) (Spray Application)

On day 0, gerbils are treated with the respective test compound at a given dose by spray application. On day +1 (+2), the animals are infested with nymphs of *R. sanguineus*. Ticks are left on the animals until full repletion. Seven days after infestation nymphs dropped off fully engorged are collected and counted. Efficacy in killing is expressed as a tick number reduction in comparison with a placebo treated group, using the Abbot's formula.

In this test the racemic compound of formula (I) according to the present invention showed 87% efficacy at a dose of 1.0 mg/kg animal biomass. The racemic compound No. 1.48 according to WO2010/070068 showed only 77% efficacy at said concentration of 1.0 mg/kg animal biomass.

EXAMPLE 5

Activity in Vivo Against *Rhipicephalus sanguineus* Ticks (Dog Tick) on Rabbits On day 0, rabbits are treated with the test compound at a given dose by spray application on their ears only. On day +1, the animals are infested on their ears with adult *R. sanguineus* ticks (sex ratio 1:1). Evaluation of efficacy is performed 24 h, 48 h, and 72 h after infestation by counting the numbers of dead and live ticks recovered from the animals. Efficacy is expressed as comparison with a placebo treated group using the Abbot's formula. Infestations can be repeated at weekly intervals until efficacy drops.

The racemic compound of formula (I) according to the present invention and the racemic compound No. 1.48 according to WO2010/070068, page 47 were tested at different concentrations in order to determine the threshold concentration where the efficacy drops below 90%.

In this test the threshold concentration for the racemic compound No. 1.48 according to WO2010/070068 was 15mg/m², where the efficacy dropped to 82%. By contrast, the racemic compound of formula (I) according to the present invention showed 93% efficacy at 7.5 mg/m² and dropped below 90% efficacy only at a concentration of 3 mg/m² (73% efficacy).

EXAMPLE 6

Activity in Vivo Against Copepodids (*Lepeophtheirus salmonis*)

The study used two groups of 45 Atlantic salmon (*Salmo salar L.*), each, with an average weight of 400 g per fish. Fish were challenged with sea lice copepodids *Lepeophtheirus salmonis*) (Cohort I). When cohort I reached pre-adult stage, all fish were challenged with a second cohort of sea lice copepodids (Cohort II).

Treatment was initiated when sea lice in cohort I became pre-adult/adults and sea lice in cohort II were early chalimus stages:

One group was treated with medicated feed-pellet containing the (S)-enantiomer of the compound of formula (I) at 1 mg/kg/day, during 7 consecutive days. One group was a placebo control group. The medicated pellets were prepared by dry coating commercially available fish feed pellets with a pre-mix containing the (S)-enantiomer of the compound of formula (I) to reach a content of 0.02% (w/w) active ingredient in the fish feed.

Sea lice were counted 10 days after treatment end. The (S)-enantiomer of the compound of formula (I) according to the present invention showed 100% efficacy at the given dose.

We claim:
1. A compound of the formula

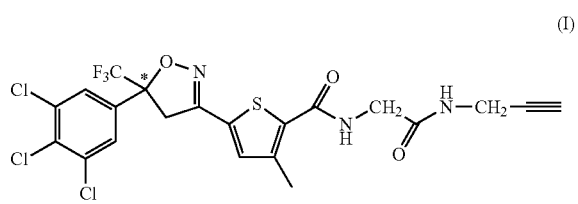

or an N-oxide or salt thereof.

2. The compound of claim 1 which is

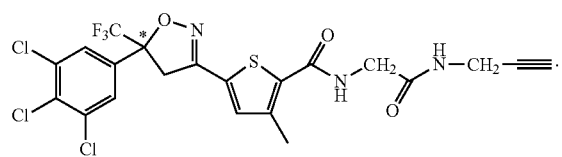 [SMILES: C#CCNC(=O)CNC(=O)c1sc(C2=NOC(c3cc(Cl)c(Cl)c(Cl)c3)(C(F)(F)F)C2)cc1C]

3. The S-enantiomer of the compound, an N-oxide or salt according to claim 1.

4. The S-enantiomer of the compound according to claim 3.

5. A composition comprising a compound, an N-oxide or salt according to claim 1 and one or more pharmaceutically or veterinary acceptable excipients.

* * * * *